Figure 2:
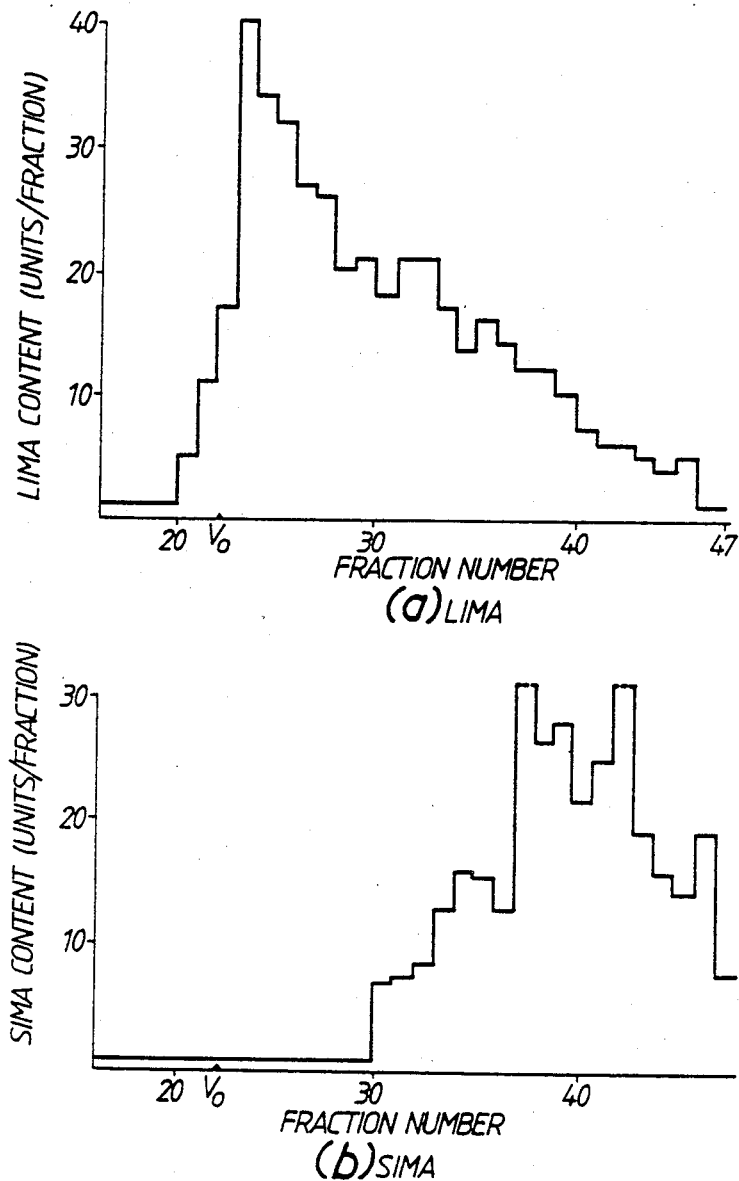

United States Patent [19]

Linnane

[11] Patent Number: 4,818,682

[45] Date of Patent: Apr. 4, 1989

[54] IN VITRO DETECTION OF GASTROINTESTINAL CANCER

[75] Inventor: Anthony W. Linnane, Camberwell, Australia

[73] Assignee: Mucan Diagnostics Pty., Ltd., Victoria, Australia

[21] Appl. No.: 860,223

[22] PCT Filed: Jun. 21, 1985

[86] PCT No.: PCT/AU85/00136

§ 371 Date: Apr. 24, 1986

§ 102(e) Date: Apr. 24, 1986

[87] PCT Pub. No.: WO86/00414

PCT Pub. Date: Jan. 16, 1986

[30] Foreign Application Priority Data

Jun. 25, 1984 [AU] Australia .............................. PG5672

[51] Int. Cl.$^4$ .............................................. C12Q 1/00
[52] U.S. Cl. ........................................ 435/7; 435/4; 436/64; 436/512; 436/543; 436/545; 436/813
[58] Field of Search ............... 435/4, 7; 436/543, 545, 436/813, 64

[56] References Cited

U.S. PATENT DOCUMENTS

4,579,827  4/1986  Sakamoto et al. .................. 436/813

OTHER PUBLICATIONS

Ma et al.–Chem. Abst., vol. 93 (1980), p. 5520z.
De Boer et al.: Br. J. Cancer (1980), 40, 325.
Pihl et al.; Pathology (1980), 12, pp. 439–47.
De Boer et al.; Histopathology 1981, 5, 295–303.
De Boer et al.; Pathology (1981), 13, pp. 547–55.
Ma et al.; Aust. N.Z. Surg., vol. 52–No. 1, Feb. 1982, pp. 30–34.
Ma et al.; American Cancer Society, Apr. 15, 1982, vol. 49, No. 8, pp. 1664–1667.
Ma et al.; Pathology (1983), 15, pp. 385–91.
Nayman et al.; Japanese Journal of Surgery, vol. 13, No. 4, pp. 317–323, 1983.
Gold et al.; McGill University Medical Clinic, 1965, pp. 467–481.
Mackay; Royal Melbourne Hospital, pp. 254–264.
Cheek et al.; The Medical Journal of Australia, Aug. 22, 1981, p. 201.
Gold et al.; The Medical Journal of Australia, Aug. 22, 1981, p. 170.
Phil et al.; Pathology (1980), 12, pp. 7–13.
Herlyn et al.; Proc. Natl. Acad. Sci., U.S.A., vol. 76, No. 3, pp. 1438–1442, Mar. 1979.
Koprowski et al.; Science, vol. 212, Apr. 3, 1981, pp. 53–54.
Magnani et al.; Science, vol. 212, Apr. 3, 1981, pp. 55–56.
Del Villano et al.; Clin. Chem. 29/3, 549–552 (1983).
Sears et al.; Journal of Clinical Immunology, vol. 2, No. 2, 1982.
Magnani et al.; Cancer Research 43, 5489–5492, Nov. 1983.
Friguet et al.; Journal of Immunological Methods, 60 (1983), 351–358.
Trevelyan et al.; Distillers Co. Ltd., pp. 298–303, 1950.

*Primary Examiner*—Sam Rosen
*Attorney, Agent, or Firm*—Cushman, Darby & Cushman

[57] ABSTRACT

An in vitro diagnostic method for detecting the presence in a patient of cancer cells or other cells producing mucin antigens comprises the step of testing a sample of a physiological fluid, particularly a sample of blood, blood serum or blood plasma, taken from the patient to detect the presence of small intestine mucin antigen (SIMA) and/or large intestine mucin antigen (LIMA) in the sample. An in vitro diagnostic kit is also disclosed.

7 Claims, 8 Drawing Sheets

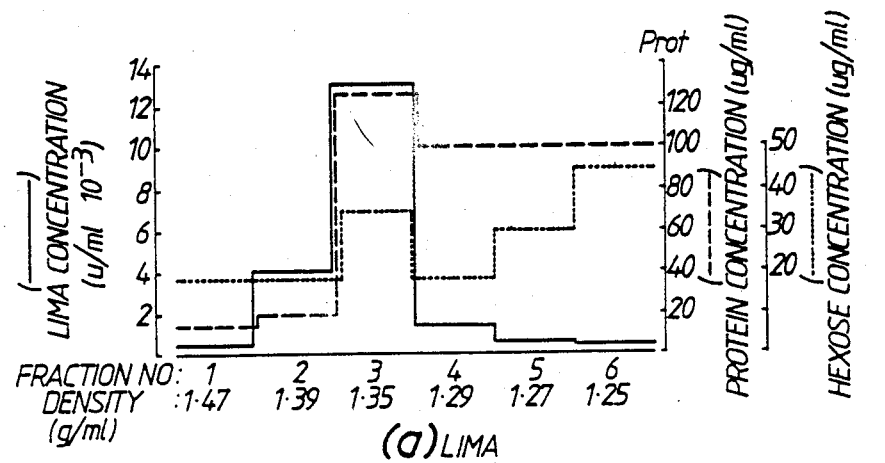
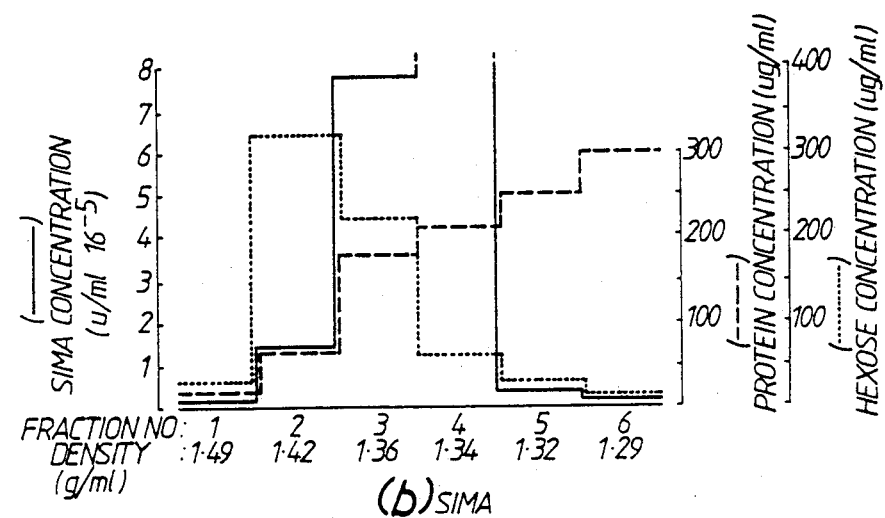
FIG.1.

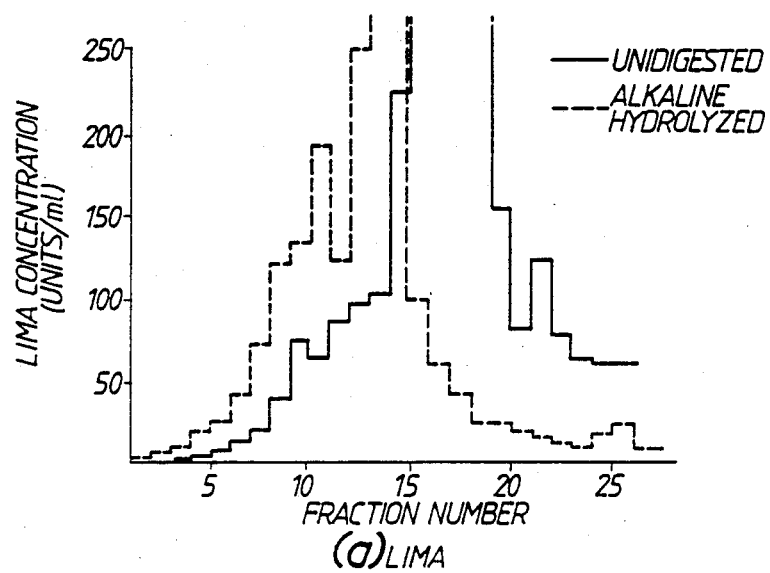
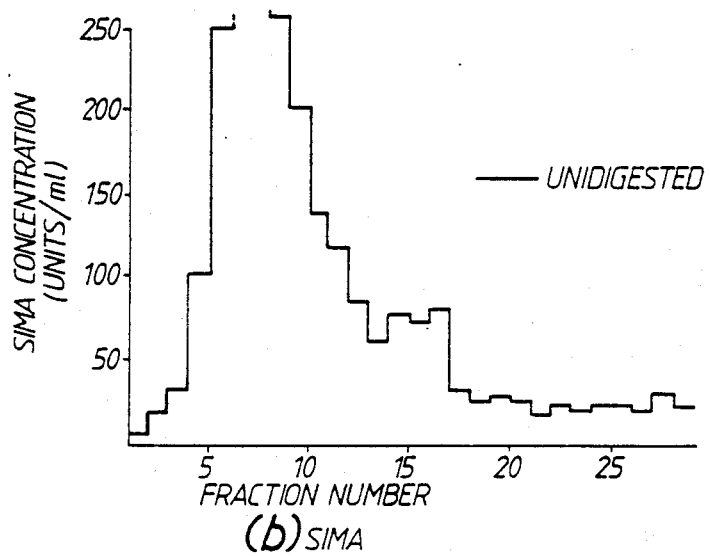
FIG. 3.

1. COAT WELLS WITH ANTIGEN. (MUCIN)

WASH.

2. INCUBATE MONOCLONAL ANTIBODIES WITH STANDARD MUCIN SOLUTIONS OR TEST SAMPLES.

Ab ALONE    Ab+MUCIN

3. ADD ANTIBODY MIX (2) TO COATED WELL (1).

WASH.

4. ADD ENZYME-LABELLED SECOND ANTIBODY (SHEEP ANTI MOUSE).

WASH.

5. ADD SUBSTRATE AND DEVELOP COLOUR

+ SUBSTRATE    + SUBSTRATE

6. READ O.D.

3+ COLOUR    1+ COLOUR

7. CALCULATE % INHIBITIONS.

STANDARD CURVE.

CALCULATE RESULTS.

100% REACTION (i.e. NO ADDED Ag) = 0% INHIBITION

DECREASED REACTION = 67% INHIBITION

COMPETITIVE ELISA ASSAY

FIG.5.

1. COAT THE MICROLITRE PLATE WELLS WITH MONOCLONAL ANTIBODY (Ab).

2. CONCURRENTLY WITH STEP 1, ADD MUCIN ANTIGEN TO TO A PREPARATION OF THE SAME MONOCLONAL ANTIBODY WHICH HAS BEEN LABELLED WITH $^{125}I$ (L).

3. ADD MIXTURE FROM STEP 2 TO WELLS COATED IN STEP 1.

4. WELLS COUNTED TO DETERMINE $^{125}I$ BOUND.

TWO-SITE SANDWICH RADIO-IMMUNOASSAY

 1. COAT PLATE WITH MONOCLONAL
ANTI-LIMA ANTIBODY (Y)
WASH.
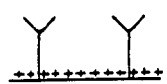 2. BLOCK PLATE WITH BOVINE
SERUM ALBUMINE.
WASH.
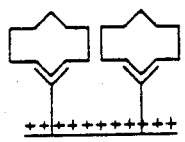 3. ADD SERUM (LIMA STANDARD) (⇔)
LIMA BOUND TO ANTIBODY.
WASH.
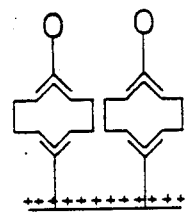 4. ADD ALKALINE PHOSPHATASE-LABELLED
MONOCLONAL ANTI-LIMA ANTIBODY (⅄)
WASH.
5. ADD ENZYME SUBSTRATE
(P-NITROPHENYL PHOSPHATE)
COLOUR DEVELOPMENT.
6. READ OPTICAL DENSITY.
ENZYME IMMUNOASSAY OF LIMA
*FIG.7*

IN VITRO DETECTION OF GASTROINTESTINAL CANCER

This invention relates primarily to methods and systems for the diagnosis of mucinous cancers, particularly cancer of the gastrointestinal tract, as well as cancer of the breast, lung, stomach, ovary, and the like.

The mortality due to cancer of the intestinal tract ranks second only to that of lung cancer in men and breast cancer in women. Although much attention has been paid to these conditions, the death rate has not been significantly reduced in recent years. Early detection is essential for improvement to occur in the survival figures. Cancer cells at times produce substances which are undetectable or found only in very low levels in healthy individuals. This feature can be used to develop innovative diagnostic techniques. Tests aimed at detecting these cancer-associated substances are of great assistance in the differentiation between individuals with cancer in comparison with healthy individuals.

Carcinoembryonic antigen (CEA) is the most extensively investigated antigen associated with gastrointestinal cancer and indeed the most studied of all tumour-associated antigens. This antigen is present in the human fetal gastrointestinal tract, but is not present or is present at only low levels in the normal adult colon. CEA was first demonstrated in human colonic cancers by Gold and Freedman in 1965.[9] CEA was present in the blood of such cancer patients and therefore intially regarded as an oncofetal antigen which gave great hope for the early diagnosis of cancer of the human digestive system. Subsequently it has been shown that assay of CEA in blood is not specific enough to be of value for the early diagnosis of gastrointestinal cancer because it is often elevated in a number of non-neoplastic conditions including smokers' bronchitis and liver disease.[10] For instance, 10% of the normal population shows false positive results, in the sense that these individuals have elevated blood CEA levels although they do not have cancer or even benign tumours. Secondly, CEA is often undetectable even in patients with rather large tumours,[11-13] i.e. there is a considerable false negative rate (about 50% of patients with gastrointestinal cancer do not show increased blood CEA levels). Despite these limitations, however, CEA assay is still of considerable value in preoperative assessment and postoperative management of cancer patients. CEA assays account for about 40% of current cancer tests.

Alpha fetoprotein (AFP) is another oncofetal antigen found in high levels in the fetus but not in normal adults. Increased blood levels of AFP are present in patients with primary liver cancer, secondary tumours of the liver, the majority of cases of some types of testicular cancer (teratoma); but also in toxic liver injury and cirrhosis. Despite this apparently limited usefulness, AFP represents about 20% of currently performed cancer tests.

Recently, monoclonal antibody-based radioimmunoassays for the measurement of the tumour-associated antigen CA 19-9 TM, have become commercially available[14-19]. This CA 19-9 TM assay is claimed to have high sensitivity and specificity for all stages of pancreatic cancer, however, with respect to the detection of colorectal cancer, this assay seems to have low sensitivity.

In 1980, a new mucin glycoprotein antigen was isolated from cancer of the large bowel.[1] This substance is also present in normal adult small intestine and has therefore been named "small intestine mucin antigen" (SIMA). SIMA was shown to be an oncofetal antigen, in that in the 8-12 week old fetus it is found throughout the gastrointestinal tract, by the time of birth is no longer detected in normal circumstances other than the small intestine, but SIMA is found in cancer of many parts of the gatrointestinal tract and other organs. Another mucin substance, referred to as "large intestine mucin antigen" (LIMA) has also been isolated from normal large intestine. LIMA has also been shown to be an oncofetal antigen, and is produced to a varying extent by a number of cancers. Extensive immunohistological studies have shown that LIMA is antigenically different from SIMA and both are also distinct from CEA. These intestine-associated mucin antigens have also been detected in some tumours of the stomach, gall bladder, lung, breast, and ovary, as well as in premalignant conditions of the above organs. (Refs. 1-8).

Results of immunohistochemical staining, using anti-SIMA and anti-LIMA monoclonal and polyclonal antibodies, of normal fetal and adult tissues, and cancers of various organs are shown in Table 1.

TABLE 1

| SUMMARY OF SIMA AND LIMA DISTRIBUTION IN HUMAN TISSUES - IMMUNOHISTOCHEMICAL STUDIES. | | |
|---|---|---|
| | SIMA | LIMA |
| Fetal Tissues (8-40 weeks) | | |
| stomach | + | + |
| small intestine | + | − |
| large intestine | | |
| 8-12 weeks | + | − |
| 13-40 weeks | − | + |
| Normal Adult Tissues | | |
| stomach | − | − |
| small intestine | + | − |
| large intestine | − | + |
| gall bladder | − | − |
| ovary | − | − |
| breast | − | − |
| lung carcinoma | − | + |
| Cancers | | |
| colon carcinoma | + | + |
| stomach carcinoma | + | + |
| ovary carcinoma | + | + |
| gall bladder carcinoma | + | + |
| breast carcinoma | + | − |
| lung | − | + |

It has now been discovered, for the first time, that despite the high molecular weight of these mucinous glycoproteins, SIMA and LIMA can be detected in the blood serum of a high proportion of patients with large intestinal cancer by the use of diagnostic antibody assays. SIMA and LIMA are not found in measurable quantities or are found in very low quantities in the blood sera of healthy controls. Initial studies involving a small group of cases already show that the combination of SIMA and LIMA tests can be used to detect about 80% of patients with colorectal cancer, whereas use of CEA tests alone detect only about 56% of such cancers. These SIMA and LIMA assays are also more sensitive than CEA assays in the detection of Stage B and C (Duke's classification) cancers. In addition, LIMA can be detected in the blood of a high proportion of patients having ulcerative colitis of the colon. Such patients commonly develop large bowel cancer. Similarly, SIMA and LIMA can be used to detect the existence of pre-cancerous states.

As used throughout this specification, the terms SIMA and LIMA are used to denote not only the mucin antigens described in greater detail below, but also parts thereof which are antigenically related thereto and which may exist in physiological fluids, particularly blood serum or plasma.

According to the present invention there is provided an in vitro diagnostic method for detecting the presence in a patient of cancer cells or other cells producing mucin antigens, which method comprises the step of testing a sample of a physiological fluid taken from the patient to detect the presence or absence of SIMA and/or LIMA in said sample.

Preferably, the said method comprises the steps of contacting a sample of a physiological fluid taken from the patient with monoclonal or polyclonal antibodies to SIMA and/or LIMA or fragments of said antibodies, or said antibodies or fragments thereof labelled with a label capable of providing a detectable signal, and detecting the presence of the binding of said antibodies or fragments thereof, or said labelled antibodies or fragments thereof, to their corresponding antigen.

Particularly preferred physiological fluids for use in these diagnostic methods are blood, blood serum or plasma.

In yet another aspect, there is provided an in vitro diagnostic kit or system for detecting the presence in a patient of cancer cells or other cells producing mucin antigens, which kit or system comprises means for detecting the presence of SIMA and/or LIMA in a sample of a physiological fluid taken from the patient.

In one particular aspect of this invention, there is provided an in vitro diagnostic kit or system for detecting the presence of SIMA and/or LIMA in a sample of a physiological fluid, such as blood or blood serum, taken from the patient, the kit or system comprising monoclonal or polyclonal antibodies capable of immunoreaction with SIMA and/or LIMA, or fragments thereof, together with indicator means for indicating the presence of an immuno reaction between said antibodies and their corresponding antigens.

In a particular embodiment of this aspect of the invention, the diagnostic system further comprises a component thereof linked to a solid support, said component comprising either (i) SIMA and/or LIMA, or (ii) said antibodies capable of immunoreaction with SIMA and/or LIMA.

This aspect of the present invention includes a number of embodiments utilising different forms of indicator means. In one aspect of the invention, the indicator means comprises a label capable of providing a detectable signal, said label being bonded to said antibodies capable of immunoreaction with SIMA and/or LIMA. In another aspect, however, the indicator means comprises a label capable of providing a detectable signal, said label being bonded to second antibodies, said second antibodies being raised to said first named antibodies and indicating the presence of said immunoreaction by bonding to said first named antibodies. In a further aspect, the indicator means may comprise Staphylococcal Protein A having a label bonded thereto. The labels used in any of these embodiments may comprise known enzymes, radioactive, elements, fluorescent chemicals or compounds such as biotin.

The use of immunoassays for SIMA and LIMA has enabled the detection of these mucin antigens in all stages of colorectal cancer. These results therefore establish this system as being potentially more useful and valuable than the CA 19-9 TM or CEA assays discussed above.

Whilst the present invention is primarily directed to the detection of mucinous cancers, it will also be appreciated that the immunoassays for SIMA and LIMA are of value in the detection of inflammatory conditions such as ulcerative colitis or gastric ulcers, as well as in the detection of pre-cancerous states.

As will be apparent from the foregoing description, the mucin antigens SIMA and LIMA referred to herein can be characterised firstly by the source from which they are isolated (using methods described in detail below). Further characterisation and identification of these antigens can be achieved by use of polyclonal and monoclonal anti-SIMA and anti-LIMA antibodies, and by immunohistochemical techniques, using, for example, "competitive" immunoassay techniques to detect antigenic activity by inhibition of binding of anti-SIMA or anti-LIMA antisera to specific gastrointestinal tissues.

Further details of the present invention will be discussed below. It is noted, however, that immunoassays for SIMA and/or LIMA in accordance with the present invention provide a highly sensitive diagnostic tool for the detection of cancer cells or other mucin antigen producing cells in a patient, in particular in the pre-operative workup of cancer patients in order to obtain an indication of the extent of tumour load, and to obtain a base value for post-operative follow-up of patients treated surgically, or by any other modality (e.g. radiotherapy, chemotherapy) in order to detect recurrence at a treatable stage, or to monitor treatment efficacy. In such applications, the diagnostic system of the present invention may initially be combined with immunoassays for CEA or other known tumour-associated antigens, which are currently being used in these situations. In addition, the SIMA/LIMA (optionally in combination with CEA) diagnostic systems may be applied to the screening of populations at high risk for developing intestinal cancer, e.g. patients with ulcerative colitis or gastric ulcers, an area where CEA diagnostic systems alone have, after initial testing, been found to have no diagnostic value.

In work leading to the present invention, several monoclonal antibodies have been produced by immunizing mice with mucin preparations extracted from large bowel cancer. Immunohistochemical staining of tissues was used to classify 5 of these monoclonal antibodies as anti-SIMA (reacting with normal small intestine and large intestinal cancer) and 5 as anti-LIMA (reacting with normal large intestine and large intestinal cancer). Immunochemical analyses showed that the affinities of the antibodies vary by as much as 100-fold in each class.

The following examples illustrate the production and characterisation of mucin antigens, methods currently used in the production of polyclonal and monoclonal antibodies to SIMA and LIMA, and the use of those monoclonal antibodies in in vitro diagnostic methods for the detection of the presence of cancer or other mucin antigen producing cells in a patient in accordance with the present invention.

EXAMPLE 1

A. Purification and Characterisation of Mucin Antigens

Mucins were extracted from surgical specimens obtained from excision of colorectal cancer tissue. Areas of normal large bowel distal to the tumour were obtained from tissue removed with the tumours, and were examined by light microscopy to confirm their normal appearance prior to use. Samples of normal duodenum, jejunum, and colon, were also obtained as autopsy from accident victims. Mucins were extracted from samples of colonic cancer (LIMA and SIMA), normal large intestine (LIMA), or normal duodenum or jejunum (SIMA) by the procedures outlined below.

The mucin preparation used for immunizing mice for monoclonal antibody production and screening was prepared from a cancer specimen diagnosed histologically as a "partly mucinous" adenocarcinoma of the sigmoid colon. The tissue specimen (approx. 5 g) was cut into small pieces, then homogenized in 10 volumes of 4M guanidine hydrochloride containing 24 mM EDTA, 10-mM N-ethylmaleimide and 1 mM benzamidine HCl. Following centrifugation at 20,000 xg for 20 min, the pellet was re-extracted with fresh guanidine hydrochloride. The mucin in the pooled supernatants was then adjusted to a density of 1.35 g/ml with caesium chloride and centrifuged at 105,000 xg for 64 hr. The resulting gradient was separated into 6 equal fractions ranging in density from 1.25 to 1.55 g/ml. Each fraction was dialysed against distilled water and assayed for protein (modified Bradford assay) and hexose 21, as well as for antigenic activity by determining its ability to inhibit specific immunofluorescent staining of gastrointestinal tissues by anti-SIMA and anti-LIMA antibodies, and by immunoassays using monoclonal antibodies (see below for details). The fraction containing the highest antigenic activity is re-fractionated on CsCl gradients, and the fractions assayed as described above.

(i) LIMA

LIMA was found in the bottom 2 or 3 fractions of the gradient with a density of 1.34 to 1.55 g/ml. The LIMA preparations were polydisperse but usually found in highest antigenic activity at about 1.4±0.08. Antigenic activity, hexose and protein content of each fraction of a typical third CsCl gradient centrifugation of a LIMA preparation are shown in FIG. 1a. The hexose/protein ratios (wt/wt) for fractions 2 and 3 were 0.5 and 0.25 respectively. The peaks of hexose, protein and antigenic activity did not coincide; fraction 3 contained most of the antigenic activity. The overall yield of LIMA from a typical experiment, determined by enzyme-linked immunoassays (EIA) is about 35% of that present in a tissue homogenate. The overall purification of LIMA is of the order of 1000-fold. SIMA is not usually detected in LIMA preparations from normal large bowel. The successful use of LIMA preparations in sandwich immunoassays (where the same monoclonal antibody must bind more than once to the molecule), indicates that the antigenic determinant which is recognised by the monoclonal antibodies must be repeated at least twice on the molecule.

The high molecular weight of LIMA was indicated by its ability to penetrate into 7% polyacrylamide electrophoresis gels. Further studies using gel filtration chromatography showed that the LIMA antigen eluted in the void volume of Sepharose 6B (which separates globular proteins in the approximate molecular weight range: $1 \times 10^4 - 4 \times 10^6$, and dextrans of molecular weight: $10^4 - 10^6$—Pharmacia catalogue specifications) and Sepharose 2B (fractionates globular proteins of M.W. range $7 \times 10^4 - 4 \times 10^7$, and dextrans in the range: $10^5 - 2 \times 10^7$). Gel-chromatography of LIMA on Sephacryl 1000 column (1 cm×65.5 cm) eluted in 10 mM phosphate buffered saline (separates dextrans of M.W. range: $5 \times 10^5 - 10^8$), is shown in FIG. 2a. The majority of the LIMA antigenic activity was included in this matrix and eluted as a broad peak which may indicate polydispersity of the LIMA preparation. A similar degree of polydispersity is seen with many other proteoglycan molecules, and may arise, for example, from variations in structure or a aggregation which affect the M.W. but not the antigenicity of such molecules.

In order to better estimate the size of the LIMA, a number of preparations were subjected to ultracentrifugation on glycerol gradients (10% to 20%) in order to determine sedimentation coefficients (Beckman SW 50 Ti rotor, 22,000 rpm×15 h or 42,000 rpm×5 h at 4° C.). The gradients were fractionated and each fraction assayed for antigenic activity in a sandwich assay. A typical LIMA gradient is shown in FIG. 3a. From this and other runs, weighted averaged s values were determined according to the following equation:

$$S = \frac{lnRt - lnRo}{\omega^2 \times t} \times \frac{10^{13}}{3600}$$

where $\omega$ is the angular velocity, t is the time of centrifugation (hours), Ro is the radius of rotation to the top of the gradient and Rt is the weighted averaged radius to which the peak of antigenicity had moved. The mean s values calculated from several different experiments was 9.5±1.5.

LIMA was subjected to a number of different physical, chemical and enzymic treatments in order to gain further information about the nature of the antigen; these are summarized in Table 2. The antigenicity of LIMA in a sandwich assay was stable to storage for at least 1 month at 40° C. or for up to 5 min. at 100° C. Boiling for 10 min. or longer resulted in a 40% loss in activity. This stability of LIMA to boiling suggests this antigen may be an extensively glycosylated molecule, and that the epitope involves or is protected by carbohydrate. Alkaline treatment of LIMA to cleave 0-glycosidic linkages between carbohydrates and protein was performed at several concentrations of KOH: 0.01M, 0.05M, 0.10M, 0.25M, 0.50M (at 4° C. for 2, 4 or 16 h) whereafter 85%, 70%, 70%, 55% and 45% respectively of antigenic activity remained after treatment. Addition of a nucleophile such as 2-mercaptoethanol (0.1M) enabled the β-elimination reaction to be performed under milder conditions (0.01M, KOH, at 4° C. for 4 h), with a resultant loss of 55% of the antigenic activity. In addition to the partial loss of antigenic activity resulting from alkaline treatment of LIMA, analysis on glycerol gradients showed a significant reduction in the weighted averaged s value (5.5) indicating a decreased molecular weight (FIG. 3a). Attempted reduction of LIMA (in 6M guanidine HCl, 0.5M Tris pH8.1, 0.002M EDTA, 10 mM dithiothreitol, at 50° C. for 2 h, 4 h or 16 h followed by alkylation with 0.4M iodoacetic acid at 4° C. overnight) had no significant effect on antigenic activity.

Digestion experiments with a number of highly purified enzymes were performed to determine the chemical nature of the LIMA antigen. After treatment the samples were boiled for 5 min. or neutralized (pepsin) to inactivate the enzymes prior to immunoassay. Neither pepsin nor clostripain, (tested at several enzyme concentrations incubated with LIMA for 2, 4 or 16 h) showed any significant effect on antigenic activity of LIMA (Table 2). Papain digestion (0.01 or 1.0 mg/ml) of LIMA resulted in a significant loss of antigenic activity with only 20% of activity remaining after 2, 4 or 16 h of digestion, when assayed in a sandwich assay. When assayed in a competitive ELISA (where the assay is not dependent on the multivalency of epitopes on the antigen) the activity remaining after 2 h digestion with papain was 75, after 4 h - 65% and after 16 h - 35%. This implies that under mild conditions of papain digestion, LIMA may be degraded into fragments most of which have only one epitope and are therefore not detected in a sandwich assay, but are detected in a competitive assay. This result establishes that the antigen has a degree of susceptibility to papain, yet is essentially resistant to pepsin and clostripain.

(ii) SIMA

SIMA was found in 2 or 3 fractions of the gradient with a density between 1.29 and 1.45 g/ml. The SIMA preparations were polydisperse but the majority of antigenic activity was usually found at a density of $1.38 \pm 0.05$. The antigenic activity, hexose and protein content of each fraction of a typical third CsCl gradient centrifugation of a SIMA preparation are shown in FIG. 1b. The hexose/protein ratios (wt/wt) for fractions 3 and 4, where the majority of the antigenic activity occurs, were 1.5 and 0.3 respectively. The yield of SIMA from a typical colonic cancer specimen is around 40%, determined by EIA. The purification achieved by these procedures is around about 1000-fold, similar to the purification of LIMA. Most colorectal cancer tissues were found to contain considerable LIMA as well as SIMA, whereas extracts from samples of normal duodenum and jejunum contained SIMA but no detectable LIMA. LIMA could be removed from "SIMA" preparations derived from a colorectal cancer specimen, by passing the mixed mucin extracts through an anti-LIMA monoclonal antibody affinity column. The identification of SIMA in the preparation is based on reaction with monoclonal antibodies and inhibition of immunofluorescent staining of small intestine by polyclonal and monoclonal antibodies. As described for LIMA, the use of SIMA in a sandwich immunoassay indicates the existence of a repeated epitope on the antigen molecule.

Figure 4:
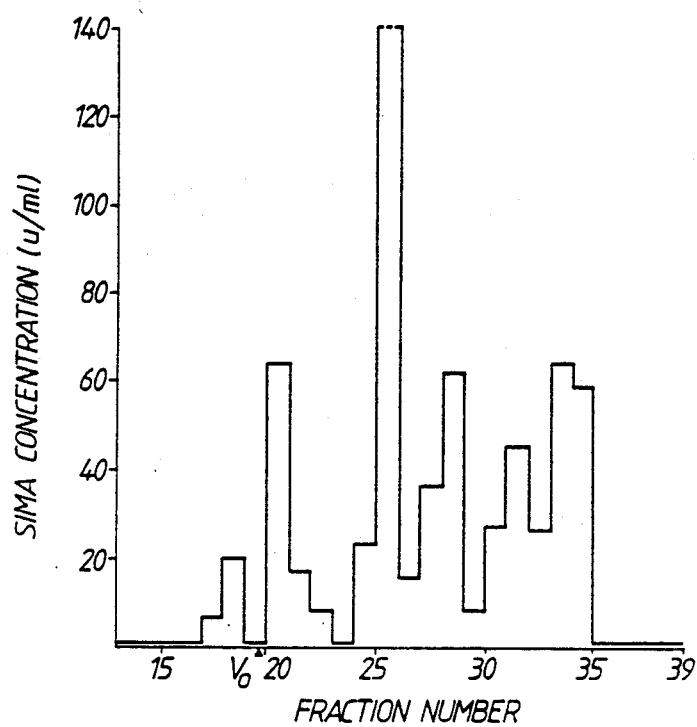

As was the case with LIMA, SIMA did not penetrate 7% polyacrylamide electrophoresis gels. However analysis of gel filtration on Sepharose 2B column (1.5 cm×7 cm), eluted in 25 mM Tris pH 8.0 containing 4M guanidine HCl, showed that SIMA was included in the gel and was polydisperse, eluting into a number of peaks (FIG. 4), and was of much smaller molecular weight than LIMA. SIMA was also run on a Sephacryl 1000 column, and again eluted as a broad peak of much lower molecular weight than the over-all LIMA preparation (cf FIGS. 2a and b).

The s values were determined for a number of SIMA preparations on 10% to 20% glycerol gradients as described above for LIMA. A typical SIMA gradient is shown in FIG. 3b. This means s value calculated from a number of experiments was $4.8 \pm 1.4$, which is much lower than the values for LIMA.

SIMA was found to be more stable to alkaline treatment and boiling, than LIMA. No significant alteration in antigenic activity was observed, using conditions as described above for the alkaline treatment of LIMA. In addition, SIMA antigenic activity was not significantly affected by boiling for 5 min., and only 6% of activity was lost after boiling for 10 min. (see Table 2).

SIMA was digested with a number of highly purified enzymes as described above for LIMA (Table 2). Clostripain had no effect on antigenic activity of SIMA as assayed in a sandwich EIA. Digestion of SIMA with papain for 2 h. had no effect, whereas 50% of antigenic activity was lost after 16 h. of digestion. Pepsin digestion of SIMA resulted in a 70% loss of antigenic activity, which contrasted with LIMA which was resistant to pepsin (10 μg/ml pepsin at room temperature overnight).

TABLE 2

EFFECTS OF VARIOUS DEGRADATION PROCEDURES ON MUCIN ANTIGENS

| TREATMENT | PERCENT ACTIVITY REMAINING AFTER TREATMENT | |
|---|---|---|
| | LIMA | SIMA |
| Boiling (10 min) | 60 | 94 |
| Alkaline treatment | 45 | 100 |
| Pepsin digestion | 100 | 30 |
| Papain digestion 2 h. | 20 | 100 |
| Papain digestion 16 h. | 20 | 50 |
| Clostripain digestion | 100 | 100 |
| Disulphide reduction | 100 | Not done |

A number of refinements may be introduced into the mucin purification procedure as follows:

1. Perchloric acid (1M), treatment with sodium acetate and heating at 70° C., or boiling for 5 minutes may also be used to enrich the purity of the mucin preparations.

2. Repeated CsCl gradient ultracentrifugation has been demonstrated to markedly (up to 10 fold) improve the purity of the mucin preparation.

3. Monoclonal antibody affinity chromatography can be used in two ways: firstly, for example, using anti-LIMA monoclonals to remove LIMA from a SIMA preparation (and vice versa); and secondly, by using adsorption and elution of mucin (SIMA) onto anti-SIMA monoclonals to purify SIMA from other contaminating proteins.

4. Mucin antigens may also be purified from normal and cancerous tissues by the use of lectin columns, gel electrophoresis, ion exchange or gel filtration chromatography.

The various steps in the purification of mucin preparations are monitored by competitive immunohistochemistry and EIA using polyclonal and monoclonal antibodies testing to determine SIMA and LIMA composition of the preparations.

B. Production of Polyclonal Antisera

The anti-SIMA polyclonal antiserum used in these studies was that produced in rabbits by Ma et al (1980)[1]. Polyclonal antiserum that recognizes LIMA was produced by similar techniques involving the immunization of rabbits with mucin preparations extracted from normal large intestine according to Ma et al (1980)[1]. These type of antisera although relatively non-specific and cross reactive were used initially for monitoring mucin purification steps. Polyclonal antisera prepared from highly purified SIMA and LIMA may be used in "two-site" sandwich immunoassays described below.

C. Preparation of Monoclonal Antibodies

Immunization Schedule:

Female Balb/C mice, about 8 weeks old, were immunized with about 50 μg per mouse of partially purified cancer mucin preparation in 4 subcutaneous and 1 intraperitoneal injections, initially in complete Freund's adjuvant, followed about 4 weeks later by a similar set of injections in incomplete adjuvant. Approximately 12 days after the second immunization, mice were bled via the tail vein, and serum antibody titres determined by ELISA. Three weeks after the second immunization, mice with high serum titres were given booster injection by intraperitoneal injections of 10 μg of cancer mucin preparation in PBS on four consecutive days, followed by the fifth day of animal sacrifice, removal of the spleen and conventional cell fusion with mouse myeloma lens.

Cell Fusion, Hybridoma Growth, Cloning:

A spleen cell suspension was prepared from the spleen of an immunized mouse by gentle teasing in phosphate-buffered physiological (GKN) solution. $10^8$ spleen cells were fused with $5 \times 10^7$ myeloma cells [X63 Ag 8.6.5.3] (obtained from T. Stahelin, Hoffman La Roche, Basel, Switzerland) according to standard procedure. Spleen cells and myeloma cells were mixed in 50% PEG-4000 (GC grade), added slowly over 60 seconds. After standing for 90 seconds, the cells suspended in PEG were diluted slowly with 7 ml GKN solution (added over 5 mins), then diluted to approx. 300 ml in RPMI 1640 medium containing 10% fetal calf serum, hypoxanthine, aminopterin, and thymidine. The diluted cell suspension was then dispersed into 288 wells of 24-well multi-dishes containing $10^5$ peritoneal macrophages per well. The media was changed after about 7 days, and thereafter as required according to cell growth.

After scanning by EIA, hybridomas secreting antibodies to mucins, were cloned twice by limiting dilution in microtitre dishes containing peritoneal macrophages. For large-scale production of monoclonal antibodies, antibody-secreting hybridomas were grown as ascitic tumours in 8-12 week old mice primed 1-7 days earlier with 0.5 ml Pristane injected intraperitoneally. Ascites fluid was collected 2-4 weeks after injection of cells and stored at $-20°$ C. Immunoglobulins were purified from ascites fluid, as required, by Protein A-sepharose affinity chromatography.

Hybridoma Screening:

(i) EIA. Wells of polystyrene microtitre plates were coated with crude cancer mucin preparation (10 μg/ml in $HCO_3^-/CO_3^{--}$ buffer pH 9.6) for 3 hrs at 37° C. Wells were then washed 4 times in PBS/Tween. Hybridoma culture supernatants were incubated in the wells for 1 hr, when washed 4 times with PBS/Tween. Wells were then incubated with alkaline phosphatase-linked sheep anti-mouse immunoglobulin. After washing with PBS/Tween, followed by distilled water, p-nitrophenyl phosphate was added as substrate and positive wells (indicating supernatants containing antibodies to mucins) were identified as those containing the yellow product, p-nitrophenol.

(ii) Fluorescent Immunohistochemistry. "Positive" hybridomas identified by first-round screening in the EIA were then screened by immunofluorescent techniques for the ability of monoclonal antibodies produced to stain specific cells or tissues in histological sections of normal and cancerous gastrointestinal organs. Hybridoma culture supernatants were incubated on tissue sections on slides. Following blocking of non-specific binding sites with bovine serum albumin solution, tissues were incubated with fluorescein-conjugated rabbit anti-mouse immunoglobulin. Excess labelled antibody was removed by washing, and tissue section examined by fluorescent microscopy using U-V or narrow-band blue excitation.

Using the above techniques, 5 anti-SIMA monoclonal antibodies (reacting with normal small intestinal mucin and colorectal cancer mucin), and 5 anti-LIMA monoclonal antibodies (reacting with normal large intestine and colorectal cancer mucins) were identified.

Characterization of Monoclonal Antibodies

The subclass of the antibodies were determined using enzyme-coupled anti-IgG and anti-IgM antibodies (CSL). All monoclonal antibodies were found to be of the IgG subclass.

In order to fully characterize the monoclonal antibodies, their relative affinities were measured by two methods. Firstly, purified IgG was obtained for each monoclonal antibody by Protein A-sepharose affinity chromatography. The purified IgG was then titrated by EIA, and titration curves (reaction in EIA vs protein concentration) compared as a measure of the relative affinities of the antibodies. Secondly, a competitive EIA was developed (see below). The relative affinity constants were calculated using a SIMA preparation as inhibitor with the anti-SIMA monoclonal antibodies, and a LIMA preparation as inhibitor for the anti-LIMA monoclonal antibodies. The calculation of the relative affinity constants was based on the following equation:

$$Ab + Ag \rightleftharpoons AbAg$$

$$Ka = \frac{[AbAg]}{[Ab][Ag]}$$

At the concentration of antigen (mucin) which produces 50% inhibition in a competitive EIA, the concentration of free and bound antibody would be equal, i.e. [Ab]=[AbAg]. Therefore, the relative affinity constant Ka, $=1/[Ag]$. The data based on these calculations is shown in Table 3. Since the real antigen concentrations may be lower (if preparations are not 100% pure and other contaminating proteins are present), the values for Ka are minimum values and may indeed be higher.

TABLE 3

| Antibody | Relative Affinity Constant (1/mole) |
|---|---|
| Anti-SIMA Monoclonals: | |
| 4D1 | $4.2 \times 10^{10}$ |
| 4C2 | $3.3 \times 10^{10}$ |
| 3C5 | $2.4 \times 10^{10}$ |
| 4D3 | $1.6 \times 10^{10}$ |
| 2A1 | $1.0 \times 10^{10}$ |
| Anti-LIMA Monoclonals: | |
| 3B4 | $2.4 \times 10^{10}$ |
| 3D4 | $1.5 \times 10^{10}$ |
| 3C3 | $8.9 \times 10^{9}$ |
| 2D3 | $2.8 \times 10^{9}$ |
| 2C3 | $2.4 \times 10^{10}$ |

The method of Friguet et al (1983)[20] was used for determining whether each of the anti-SIMA monoclonals on the one hand, and the anti-LIMA monoclonals on the other hand, bound to the sme antigenic determinants on the SIMA and LIMA molecules, respectively. Using limiting amounts of antigen coating the plate, each antibody is titrated individually and in all possible pairings. All monoclonals produced in the current experiments were found to bind to the same or overlapping antigenic determinants on the molecule.

EXAMPLE 2

In Vitro Diagnostic Immunoassays

Two immunoassays developed for the detection of circulating mucin in blood samples are outlined below:

A. Competitive Elisa (i) The steps involved in this assay are outlined in FIG. 5. Preliminary experiments indicated that the mucin added to heparinized or EDTA treated or untreated-blood could all be recovered and quantitated in diluted plasma or serum. Undiluted plasma or serum added to the immunoassay caused interference, while no effect on assays (cf. aqueous buffers) was observed using plasma diluted 1/10. A series of blood samples from colorectal cancer patients, patients with ulcerative colitis and healthy controls were therefore assayed for SIMA and LIMA using competitive ELISA. Plasma from healthy individuals containing added SIMA or LIMA was used as standard. High levels of SIMA and/or LIMA were detected in 13/23 (about 60%) of patients with various stages of colorectal cancer, and high levels of LIMA (but not SIMA) were detected in 4/5 cases of ulcerative colitis. Neither SIMA nor LIMA was detected in blood samples from 7 healthy controls by this method.

(ii) In order to determine whether mucin could be detected at lower levels, a method was devised for extracting and concentrating mucin from plasma samples. An equal volume of 2M perchloric acid (PCA) was added to serum or plasma samples for 15 min at room temperature. The samples were centrifuged at 8,000xg for 2 min, supernatants removed and the pellets washed in twice the original sample volume of PBS, mixed and centrifuged as before. PBS was added to the combined supernatants to a final volume of $10 \times$ the original sample volume. The samples were then concentrated/dialised 10-fold in Minicon B15 concentrators (MW cut-off 15,000, Amicon Co.). The samples were then diluted to $10 \times$ original sample volume and concentrated 50-fold. The resulting PCA extract was one-fifth of the original sample volume. This sample was then assayed by competitive ELISA, as described previously. Plasma samples from healthy volunteers with various concentrations of mucin added and taken through the above procedure were used as standards. The results for SIMA assays on samples from 39 patients with colorectal cancer, 2 patients with breast cancer, 5 patients with ulcerative colitis, and 7 controls showed that SIMA antigenic activity could be detected at low levels in some control patients and at higher levels in all but 2 of the cancer patients. 60% of samples from patients with stage B colorectal cancer (defined as those cancers with no obvious spread to other organs), 91% from stage C (defined as those cancers with detectable metastases in local lymph nodes), and 86% from stage D (disseminated cancer with spread to distant organs, such as the liver) contained elevated mucin levels compared with the control range. SIMA was also detected in one blood sample obtained from a patient with stage A colorectal cancer, and 2 patients with breast cancer.

LIMA assays have only been performed on diluted serum samples, without the concentration/dialysis steps used in the SIMA assays. Only a low proportion of patients with early stages of colorectal cancer contained measurable LIMA - 11% of stage B, 29% of stage C; but a high proportion (67%) of stage D cancer patients had elevated serum LIMA levels. A very high proportion (80%) of patients with ulcerative colitis showed high levels of circulating LIMA, even with this relatively insensitive assay. So this LIMA assay might be of value in detection of inflammatory large intestinal disease.

B. Sandwich Immunoassay

The above described monoclonal antibodies can also be used in a sandwich immunoassay.

This type of assay does have a number of advantages in improving the sensitivity of the assay, and in addition it involves fewer steps than the competitive inhibition assay described above. Furthermore, the "signal" in a sandwich immunoassay (e.g. using radioactivity or an enzyme-labelled antibody-colour in the well) is directly proportional to the mucin antigen concentration, which greatly simplifies calculation and processing of the results when compared with a competitive inhibition assay.

Figure 6:
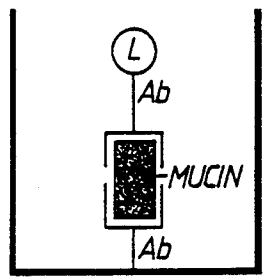

The assay comprises a solid surface coated with monoclonal antibody to immobilize the mucin molecule, and the same monoclonal antibody labelled (with $^{125}I$ or an enzyme) to detect the presence of mucin bound to the coated antibody (see FIG. 6).

a. Details of a SIMA or LIMA radioimmunoassay (RIA) (FIG. 6).

1. Wells if millititer HA plates (Millipore Corporation, USA) are coated with Protein A-purified monoclonal antibody IgG (approx. 10 $\mu$g/ml) diluted in coating buffer (sodium carbonate/bicarbonate buffer pH 9.6, 50 $\mu$l per well). Plates are incubated for 3-5 hrs at 37° C.

2. To 100 $\mu$l of serum samples or standards, add 200 $\mu$l of 0.2 M sodium acetate pH 5.0, and heat at 70°±1° C. for 15 min, then centrifuge at 9,000 xg for 10 min. The standards contain 0, 1.5, 5.0, 15, 50, 150 and 500 $\mu$/ml of SIMA or LIMA made up in pooled serum obtained from healthy volunteers.

3. $^{125}I$-labelled monoclonal antibody diluted in PBS containing 1% BSA is then added to the acetate extract supernatant (approx. 0.1 $\mu$Ci plus 100 $\mu$l supernatant), and incubated at 37° C. for 1 hr.

4. Coated wells of the millititre plates are then washed 4 times with PBS/Tween and the plates blocked for 30 min with 1% BSA in PBS at 37° C.

5. After blocking, the plates are washed 3 times with PBS/Tween. Samples (50 $\mu$l per well in duplicate wells) preincubated with $^{125}I$-labelled antibodies are then added to the wells, and incubated overnight at 4° C.

6. After overnight incubation, the wells are washed 5 times with PBS/Tween, blotted dry, and the filters at the base of each well are punched out and counted in a gamma-counter.

SIMA and LIMA levels are expressed as arbitrary units/ml, determined relative to the protein content of a reference standard of SIMA and LIMA.

A number of experiments have been performed in order to evaluate the reliability and reproducibility of the sandwich assay. Table 4 shows the variation obtained between triplicate determinations in a typical assay of control serum. For the serum assays of SIMA, the variability is highest (cr=10%) at levels of 1.5 $\mu$/ml were the assays were not considered to be reliable (therefore all values <5 $\mu$/ml SIMA are not given specific values). For serum levels of 5 to 500 U/ml SIMA the intra-assay variability is 5.6% or less.

TABLE 4
INTRA-ASSAY VARIABILITY OF SIMA RADIOIMMUNOASSAY

| Mean SIMA Concentration (U/ml) | Standard Deviation | c.v. (%) |
| --- | --- | --- |
| 1.5 | 0.15 | 10.0 |
| 5.0 | 0.12 | 2.3 |
| 50 | 2.4 | 4.7 |
| 150 | 8.4 | 5.6 |
| 500 | 17.0 | 3.4 | b. Details of a LIMA enzyme immunoassay (EIA) (FIG. 7).

1. Polystyrene microtitre plates (Nunc Immunoplates) are coated with anti-LIMA monoclonal antibody IgG (e.g. from hybridoma cell line 2C3) in bicarbonate bufferfor 3 h. at 37° C. The plates are washed twice in washing buffer (PBS/Tween/sodium azide, pH 7.2-7.6), then drained.

2. 50 µl of blocking solution (bovine serum albumin dissolved in PBS containing sodium azide, pH 7.4) is added to each well of the plate and incubated at 37° C. for 1 h.

3. To 100 µl of standard LIMA solution (standard LIMA dissolved in normal human serum, containing sodium azide, to given antigen concentrations of 0, 1.5, 5, 15, 50, 150 and 500 units per ml) or serum samples, add 200 µl of acetate extraction buffer (0.2M sodium acetate pH 5.0 containing sodium azide), and heat at 70°±1° C. for 15 minutes. Cool to room temperature and centrifuge at 10,000 xg for 10 minutes in a swing out rotor.

4. Wash microtitre plates 3 times with washing buffer and drain.

5. Add 50 µl of supernatant from acetate/heat-treated standards or serum samples to each wells (two wells per sample). Incubate the plate at 37° C. for 1 h.

6. Wash microtitre plates 4 times with washing buffer, then drain.

7. Add 50 µl per well of alkaline phosphatase-conjugated anti-LIMA monoclonal antibody, diluted 1:300 in phosphate buffered saline containing 1% bovine serum albumin. Incubate at 37° C. for 1.5 h. Wash 4 times in washing buffer, 3 times in distilled water, then drain. Add 100 µl per well of substrate (p-nitrophenyl phosphate), dissolved at a concentration of 2 mg per ml in substrate diluent buffer (0.2M sodium carbonate/bicarbonate buffer containing 0.1M magnesium chloride). Incubate at 37° C. for 20 minutes.

8. Add 100 µl per well of enzyme reaction stopping solution (0.5M sodium hydroxide).

9. Read optical density at 405 nm in a suitable microtitre plate reader.

Evaluation of Test Result (i) Construct a standard curve by plotting the mean optical density obtained for each LIMA standard (on the Y axis) versus the corresponding LIMA concentration (the X axis).

(ii) Using the mean optical density for each serum sample, determine the corresponding concentration of LIMA in units per ml, from the standard curve.

If the specimen required additional dilution (i.e. LIMA concentration >150 U/ml) to give a value which can be read on the standard curve, the value obtained from the standard curve must be multiplied by the appropriate dilution factor to give the LIMA concentration in serum.

Figure 8:
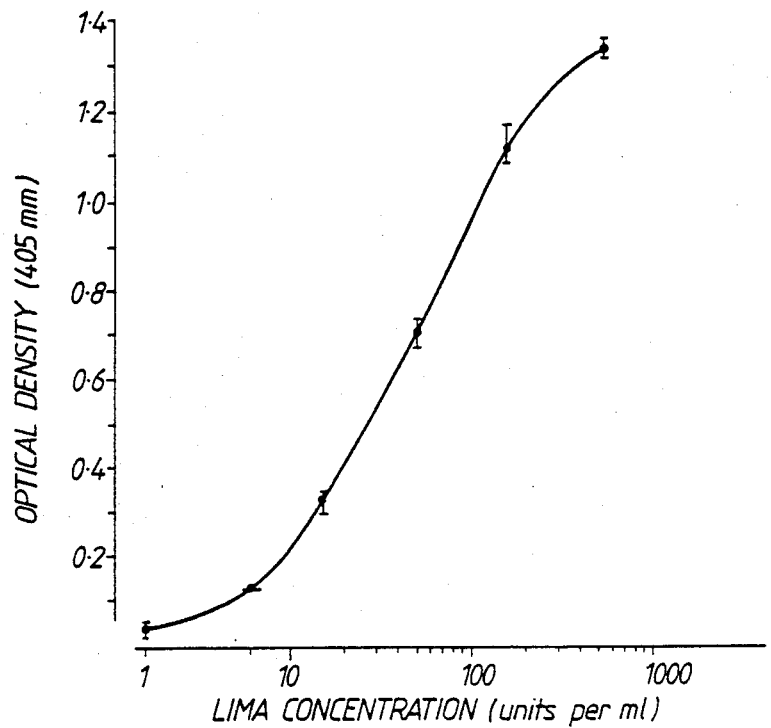

An example is given in Table 5 and FIG. 8 is constructed from data in Table 5.

TABLE 5
TYPICAL DATA FOR CONSTRUCTING A STANDARD CURVE

| Sample | OPTICAL DENSITY Duplicate | Mean | LIMA Concentration |
| --- | --- | --- | --- |
| Standard 1 | 0.012–0.010 | 0.011 | 0 |
| 2 | 0.037–0.025 | 0.031 | 1.5 |
| 3 | 0.106–0.117 | 0.112 | 5 |
| 4 | 0.293–0.340 | 0.316 | 15 |
| 5 | 0.655–0.702 | 0.678 | 50 |
| 6 | 1.057–1.138 | 1.097 | 150 |
| 7 | 1.281–1.345 | 1.313 | 500 |
| Sample 1 | 0.607–0.633 | 0.620 | 40 |
| 2 | 0.445–0.446 | 0.445 | 23 |
|  | 0.868–0.893 | 0.881 | 88 |

One example of the reproducability of the above LIMA ETA is indicated in Table 6 which shows the variation obtained between triplicate determinations in an assay of serum samples containing different amounts of LIMA. The variability is highest for values less than 1.5 U/ml (coefficient of variation 10%) or values greater than 150 U/ml (c.v. 12%). Serum levels outside these limits (i.e. <2 or >150 U/ml) are therefore considered unreliable. Samples containing >150 U/ml LIMA should therefore be diluted and reassayed.

TABLE 6
INTRA ASSAY VARIABILITY TESTS OF LIMA EIA

| Mean LIMA Concentration U/ml | Standard Deviation U/ml | C.V. (%) |
| --- | --- | --- |
| 1.5 | 0.15 | 10 |
| 5 | 0.30 | 6 |
| 50 | 3.0 | 6 |
| 150 | 7.0 | 5 |
| 500 | 6.0 | 12 | c. Clinical Results.

Table 7 below sets out a summary of results for samples from patients with various diseases and from healthy controls, showing the results of SIMA and LIMA RIA (see a. above) and CEA serum assays for the purpose of comparing the number of samples which are positive for SIMA only, LIMA only, CEA only, or any combinations of these three markers.

TABLE 7
SUMMARY OF RESULTS FROM CLINICAL TRIALS

| Diagnosis | Total No. of patients | SIMA | LIMA | SIMA LIMA | SIMA + CEA | LIMA + CEA | SIMA + LIMA + CEA | CEA | ALL NEGATIVE |
| --- | --- | --- | --- | --- | --- | --- | --- | --- | --- |
| COLON | | | | | | | | | |
| Cancer | 19 | 4 | | | 6 | | 3 | 1 | 5 |
| Colon Catarrh | 1 | | | 1 | | | | | |
| DUODENUM | | | | | | | | | |
| Ulcer | 4 | | | | | 1 | | | 3 |
| SMALL INTESTINE | | | | | | | | | |

TABLE 7-continued

SUMMARY OF RESULTS FROM CLINICAL TRIALS

| Diagnosis | Total No. of patients | Number of Patients in which Tumour Antigens were detected ||||||| |
|---|---|---|---|---|---|---|---|---|---|
| | | SIMA | LIMA | SIMA + LIMA | SIMA + CEA | LIMA + CEA | SIMA + LIMA + CEA | CEA | ALL NEGATIVE |
| Malignant Lymphoma | 3 | 1 | | 2 | | | | | |
| STOMACH | | | | | | | | | |
| Cancer | | | | | | | | | |
| -preoperative | 2 | 1 | 1 | | | | | | |
| -postoperative | 11 | | 1 | | | | | | 10 |
| -treatment unknown | 30 | 3 | 10 | 1 | | | | 1 | 15 |
| Ulcer | 6 | 1 | | | | | | | 5 |
| Malignant Lymphoma | 4 | | 3 | | | | | | 1 |
| OESOPHAGUS | | | | | | | | | |
| Gastritis | 2 | 1 | | 1 | | | | • | (post op) |
| Cancer | 3 | | | | 3 | | | | |
| GALL BLADDER | | | | | | | | | |
| Cancer | 1 | 1 | | | | | | | |
| Cholecystitis/ Gallstones | 17 | 2 | | | | | | | 15 |
| PANCREATIC | | | | | | | | | |
| Cancer | 4 | 1 | | | | | | | 3 |
| LUNG | | | | | | | | | |
| Cancer | 8 | 2 | | | 2 | 1 | | | 3 |
| BREAST | | | | | | | | | |
| Cancer | 3 | | | | | 1 | | | 1 |
| Malignant Lymphoma | 5 | 3 | | | | | | | 2 |
| Acute Lymphocytic Leukemia | 3 | 2 | | 1 | | | | | |
| HEALTHY CONTROLS | 87 | 8 | 0 | | | | | 1 | 78 |

For the purpose of this table, LIMA levels ≧10 U/ml were considered positive, CEA values ≧10 were considered positive. For SIMA serum levels ≧25 U/ml were considered positive for patients. For healthy controls samples were considered where one or more of replicate assays was ≧20 U/ml.

C. Other Immunoassay Procedures

A variation on the above "two-site" immunoassay would be to use a polyclonal anti-mucin antiserum (e.g raised in rabbits or sheep) to coat the solid phase. This would enable the use of unlabelled monoclonal antibody(s) as the "second" antibody in the assay, followed by detection of the mouse monoclonal with a labelled rabbit or sheep anti-mouse antibody. This system (or vice versa: monoclonal antibody for solid phase-coating and polyclonal antisera for detection) may provide better amplification of positive signals than when one monoclonal antibody is labelled directly.

It should also be noted that the present invention encompasses the use of a fluorogenic enzyme substrate such as 4-methylumbelliferyl (4MU)-phosphate (for alkaline phosphatase) or 4MU - β-D-galactoside (for β-galactosidase) in the sandwich immunoassays. The same enzyme-linked monoclonal antibody would be used as that in the colourmetric method described above. The expected increase in sensitivity would be about 10-fold. Other known detection systems, such as protein A, avidin-biotin, etc., may also be used. Where labelled protein A is used as the detection system in these sandwich immunoassays, then the solid phase coating antibody (whether monoclonal or polyclonal) would be an F(ab) fragment, and the detecting antibody an intact molecule containing the Fc segment. A number of different solid phases may be used with these systems in addition to the microtitre wells, such as beads of various types. In addition, membranes may be used as adsorptive surfaces for binding antigens.

REFERENCES

1. Ma, J., De Boer, W., Ward, H. A. & Nairn, R. C. (1980). "Another Oncofoetal Antigen in Colonic Carcinoma" Br. J. Cancer 41 325–328.
2. Pihl, E., Nairn, R. C., Hughes, E. S. R., Cuthbertson, A. J. & Rollo, A. J. (1981). "Mucinous Colorectal Carcinoma: Immunopathology and Prognosis" Pathology 12 439–447.
3. De Boer, W., Ma, J., Rees, J. W. & Nayman, J. (1981). "Inappropriate mucin production in gall bladder metaplasia and neoplasia—an immunohistological study" Histopathology 5 295–303. (1981).
4. De Boer, W., Ma. J. & Nayman, J. (1981). "Instestine-associated antigens in ovarian tumours: An immunohistological study" Pathology 13 547–555.
5. Ma, J., De Boer, W. & Nayman, J. (1982). "The presence of oncofoetal antigens in large bowel carcinoma". Aust. & N. Z. Journal of Surgery 52 30–34.
6. Ma, J., De Boer, W. & Nayman, J. (1982). "Intestinal mucinous substances in gastric intestinal metaplasia and carcinoma studied by immunofluoresence". Cancer 49 1664–1667.
7. Ma, J., Handley, C. J. & De Boer, W. (1983). "An ovarian tumour specific mucin antigen—immunohistological and biochemical studies" Pathology 15 385–391.
8. Nayman, J., De Boer, W. & Ma, J. (1983). "Inappropriate mucin production in Endodermal carcinoma—one point of view". Japanese Journal of Surgery 13 317–323.
9. Gold, P. and Freedman, S. O. (1965). Specific carcino-embryonic antigens of the human digestive system. J. Exped. Med., 122, 467–481.
10. Mackay, I. R. (1979). In. Immunodiagnosis of Cancer, Herberman and McIntire (eds), Marcel Dekker, N.Y. 255.
11. Cuthbertson, A. M., Hughes, E. S. R., Nairn, R. C. Nind, A. P. P. and Pihl, E. (1981). CEA testing: Is it useful in colorectal cancer? Med. J. Australia, 170.

12. Cuthbertson, A. M., Hughes, E. S. R., Nairn, R. C. Nind, A. P. P. and Pihl, E. (1981). CEA testing in colorectal cancer. *Med. J. Australia,* 201.

13. Pihl, E., McNaughtan, J., Ma, J., Ward, H. A. and Nairn, R. C. (1980). Immunohistological patterns of carcinoembryonic antigen in colorectal carcinoma. Correlation with staging and blood levels. *Pathology,* 12, 7–13.

14. Herlyn, H., Steplewski, Z., Herlyn, D., and Koprowski, I. Colorectal carcinoma—specific antigen: Detection by means of monoclonal antibodies. *Proc. Natl. Acad. Sci. U.S.A.* 76:1438, 1979.

15. Koprowski, B., Herlyn, H., Steplewski, Z. & Sears, H. F., Specific antigen in serum of patients with colon carcinoma. *Science* 212:53, 1981.

16. Magnani, J., Brocklaus, M., Smith, D., Ginsburg, V., Blaszcyk, M., Mitchell, D., Steplewsky, Z. & Koprowski, H. A monoclonal antibody defined antigen of colon carcinoma. *Science,* 212:55, 1981.

17. Devillano, B. and coll. Radioimmunometric Assay for a Monoclonal Antibody defined Tumor Markers CA 19-9 TM. *Clin. Chem.* 29:549–552. 1983.

18. Sears, H., Herlyn, J., Delvillano, B., Steplewski, Z. & Koprowski, H. A clinical evaluation of patients with colorectal cancer. *Clinical immunology,* 2, : 141, 1982.

19. Magnani, J., Steplewski, Z., Koprowski, H., & Ginsburg, V. Identification of the gastrointestinal and pancreatic cancer-associated antigen detected by monoclonal antibody 19-9 in the sera of patients as a mucin. *Cancer Research:* 43, 5489–5492, 1983.

20. Friguet, B., Djavadi-Ohaninace, L., Pages, J., Bussaro, A., & Goldberg, M. A convenient enzyme-linked immunosorbent assay for testing whether monoclonal antibodies recognise the same antigenic site. Application of hybridomas specific for the $\beta_2$-subunit of *E.coli* tryptophan synthase. *J. Immunol. Methods.* : 351–358, 1983.

21. Trerelyan, W. E. and Harrison, J. S. Studies in yeast metabolism. I. Fractionation and microdetermination of cell carbohydrates. *Biochem J.* 50:298–303, 1952.

I claim:

1. An in vitro diagnostic method for detecting the presence in a patient of cancer cells or other cells producing mucin antigens, which method comprises the step of testing a sample of a physiological fluid selected from the group consisting of blood, blood serum and blood plasma taken from the patient to detect the presence of SIMA and/or LIMA in said sample.

2. A method according to claim 1, comprising the steps of contacting said sample with antibodies to SIMA and/or LIMA or fragments thereof, and detecting the presence of the binding of said antibodies or fragments thereof to their corresponding antigens.

3. A method according to claim 1, comprising the steps of contacting said sample with antibodies to SIMA and/or LIMA or fragments thereof labelled with a label capable of providing a detectable signal, and detecting the presence of the binding of said labelled antibodies or fragments thereof to their corresponding antigens.

4. A method according to claim 2, wherein said antibodies are monoclonal antibodies.

5. A method according to claim 2 wherein said antibodies or fragments thereof are labelled with an enzyme or radioisotope.

6. A method according to claim 1, comprising the steps of:
   (i) linking antibodies to SIMA and/or LIMA, or fragments thereof, to a solid support;
   (ii) contacting said sample with said solid support; and
   (iii) detecting the presence of corresponding antigens in said sample bound to said antibodies or fragments thereof linked to said solid support.

7. A method according to claim 6, wherein said step of detecting the presence of bound corresponding antigens comprises:
   (iv) contacting said solid support with antibodies to SIMA and/or LIMA, or fragments thereof, labelled with a label capable of providing a detectable signal; and
   (v) detecting the binding of said labelled antibodies or fragments thereof to corresponding antigen bound to said solid support.

* * * * *